(12) United States Patent
Meyer et al.

(10) Patent No.: US 8,240,157 B2
(45) Date of Patent: Aug. 14, 2012

(54) CLIMATIC CHAMBER AND CONTROL METHOD THEREFOR

(75) Inventors: Michael Meyer, Stuhr (DE); Sylvia Pomorin, Bremen (DE)

(73) Assignee: Airbus Operations GmbH (DE)

( * ) Notice: Subject to any disclaimer, the term of this patent is extended or adjusted under 35 U.S.C. 154(b) by 653 days.

(21) Appl. No.: 12/227,568

(22) PCT Filed: May 22, 2006

(86) PCT No.: PCT/EP2006/004841
§ 371 (c)(1),
(2), (4) Date: Aug. 31, 2009

(87) PCT Pub. No.: WO2007/134621
PCT Pub. Date: Nov. 29, 2007

(65) Prior Publication Data
US 2010/0050666 A1    Mar. 4, 2010

(51) Int. Cl.
*F25D 17/06*    (2006.01)
(52) U.S. Cl. .............................. 62/94; 62/476
(58) Field of Classification Search ............... 62/90, 91, 62/92, 94, 476, 478, 483, 485
See application file for complete search history.

(56) References Cited

U.S. PATENT DOCUMENTS

| | | | |
|---|---|---|---|
| 1,981,164 A | 11/1934 | Carrier | |
| 2,058,919 A | 10/1936 | Sewell | |
| 3,470,702 A | 10/1969 | Koch et al. | |
| 3,744,679 A * | 7/1973 | Nitschneider et al. | 222/238 |
| 4,312,218 A * | 1/1982 | Eckles | 73/76 |
| H229 H | 3/1987 | Phillips | |
| 4,965,968 A * | 10/1990 | Kelsall | 451/99 |
| 6,205,797 B1 * | 3/2001 | Maeda | 62/94 |
| 6,662,592 B2 * | 12/2003 | Ross et al. | 62/524 |
| 6,698,218 B2 * | 3/2004 | Goth et al. | 62/175 |
| 6,751,964 B2 * | 6/2004 | Fischer | 62/94 |
| 6,988,372 B2 * | 1/2006 | Ross et al. | 62/69 |
| 7,306,654 B2 * | 12/2007 | King et al. | 95/224 |
| 7,550,122 B2 * | 6/2009 | Buczynski et al. | 422/292 |
| 8,007,717 B2 * | 8/2011 | Hill | 422/3 |
| 2002/0116934 A1 | 8/2002 | Dinnage et al. | |

FOREIGN PATENT DOCUMENTS

| | | |
|---|---|---|
| DE | 1 698 104 | 2/1968 |
| DE | 1 604 292 | 8/1970 |
| DE | 198 17 372 C1 | 4/1998 |
| DE | 10 2005 018 142 A1 | 10/2006 |
| JP | 59-129335 A | 7/1984 |
| JP | 60009800 | 1/1985 |
| JP | 61127327 | 8/1986 |
| JP | 4-115137 A | 4/1992 |
| JP | 7120025 | 5/1995 |
| JP | 07-318145 | 12/1995 |
| JP | 2005180856 | 7/2005 |

(Continued)

*Primary Examiner* — Mohammad Ali
(74) *Attorney, Agent, or Firm* — Lerner, David, Littenberg, Krumholtz & Mentlik, LLP

(57) ABSTRACT

A climatic chamber for rapidly reaching and maintaining a predetermined air humidity and/or a predetermined temperature.
The air in a sample space is conveyable by at least one fan from an outlet of sample space at least partially via a bypass branch and/or at least partially via a drying branch back to an inlet of sample space.
The air is circulated continuously by the fans in a substantially self-contained circuit. The air is guided by guide elements through the bypass branch and/or drying branch.

18 Claims, 1 Drawing Sheet

FOREIGN PATENT DOCUMENTS

| | | |
|---|---|---|
| RU | 2180421 C2 | 3/2002 |
| RU | 2223203 C1 | 2/2004 |
| SU | 287514 A | 4/1969 |
| SU | 1403027 A1 | 6/1988 |
| WO | WO-02/33391 A1 | 4/2002 |

* cited by examiner

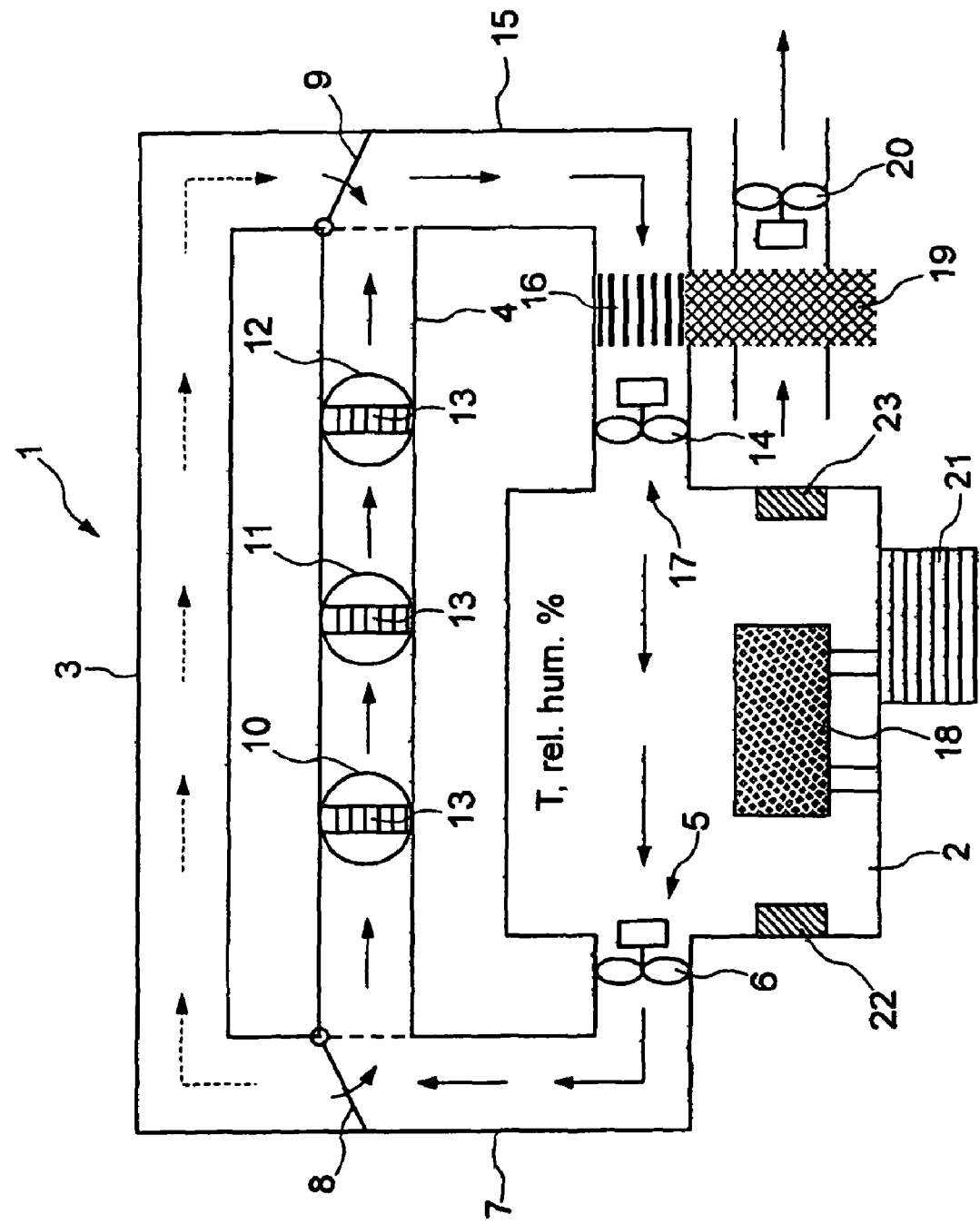

CLIMATIC CHAMBER AND CONTROL METHOD THEREFOR

FIELD OF INVENTION

The invention relates to a climatic chamber for rapidly reaching and maintaining a predetermined air humidity and/or a predetermined temperature.

The invention also relates to a method for rapidly reaching and maintaining a predetermined air humidity and/or a predetermined temperature in a climatic chamber.

BACKGROUND OF THE INVENTION

A large number of test chambers or climatic chambers for investigating material samples and suchlike are known. Defined temperatures and/or a predetermined air humidity for a specific desired climate can for example be produced in the sample space with such climatic chambers.

Bound up with the known climatic chambers, however, is the drawback, amongst other things, that a predetermined climate is established only after a relatively long time. If, however, material samples are to be subjected to a defined climate for only a short time, the material samples often cannot remain for such a long time in the climatic chamber, because the measurement results would otherwise be influenced by the excessively long dwell time in the climatic chamber.

In order to bring the material samples into the sample space after the predetermined climate has been reached, a sluice has to be provided in the climatic chamber, said sluice increasing the design outlay considerably.

On account of the generally long response times up to reaching a predetermined climate, moreover, the number of investigations to be carried out in the previously known climatic chambers is often limited.

SUMMARY OF INVENTION

There may be a need to provide a climatic chamber which avoids the drawbacks of known embodiments of climatic chambers described above.

This need may be met by a climatic chamber with the features of claim 1.

Due to the fact that the air in the sample space can be conveyed by using at least one fan from an outlet of the sample space at least partially via a bypass branch and/or at least partially via a drying branch back to an inlet of the sample space, the air humidity and/or the temperature in the sample space of the climatic chamber according to the invention may be brought very rapidly and precisely to predetermined values.

According to another exemplary embodiment of the climatic chamber, the air is conveyable by at least one guide element at least partially via the bypass branch and/or at least partially via the drying branch to rapidly reach and maintain a predetermined setpoint value for the air humidity in the sample space. An only partial diversion of the air stream into the bypass branch may thus be possible, as a result of which the air humidity in the sample space may be controlled more precisely.

According to another exemplary embodiment of the invention, provision is made such that, in order to rapidly reach and maintain a predetermined setpoint value for the temperature in the sample space, the temperature of the air can be varied by a temperature-regulating device, in particular by a heating and/or cooling device, the temperature-regulating device being arranged in particular in the region of the inlet.

The temperature-regulating device comprises a cooling device and can additionally comprise a heating device. As a result of the zeolites preferably used as a desiccant, the temperature in the sample space rises as the air humidity is absorbed by the zeolites. This rise in the temperature of the air in the sample space caused by the exothermic reaction of the zeolites with the absorption of humidity is compensated for by the cooling device, so that the air temperature in the sample space remains essentially constant. The cooling device can be constituted for example by Peltier elements or suchlike, through which the air stream to be thermally regulated passes. By the optional heating device, the temperature of the air in the sample space can, if required, be raised above the value of the ambient air temperature and/or room temperature independently of the effect of the zeolites. The heating device is preferably operated electrically, so that easy regulatability results. For example, the heating device can be constituted by helically arranged resistance wires or suchlike through which the air stream flows.

Another exemplary embodiment makes provision such that the guide element or guide elements can be actuated by a control and regulating device depending on a measured actual value of the air humidity and/or depending on a measured actual value of the temperature.

The control and regulating device may enable the predetermined air humidity values and/or the predetermined temperature values in the sample space of the climatic chamber to be reached and maintained largely automatically.

According to another exemplary embodiment, at least one air dehumidifier for drying the air is arranged in the drying branch.

The dehumidifier may enable a rapid and selective withdrawal of moisture from the air stream and thus a reduction of the air humidity in the sample space.

According to another exemplary embodiment of the climatic chamber, the air dehumidifier contains or the air dehumidifiers contain a desiccant, in particular zeolites or suchlike.

The zeolites preferably used as a desiccant may enable a rapid reduction of the air humidity and have a preferably grainy consistency. The zeolites can be accommodated for example in wide-mesh wire baskets, the cross-sectional areas whereof preferably correspond roughly to the cross-sectional area of the drying branch. The wire baskets are inserted into the air dehumidifier, so that the air preferably flows through the zeolites in the dehumidifier over the whole area. Moreover, the wire baskets in the air dehumidifiers may enable rapid replacement of the zeolites. The zeolites are capable of binding the moisture contained in the air very tightly to themselves by physical processes within the crystalline structure, but they can also be regenerated by the supply of heat after complete saturation with moisture.

According to another exemplary embodiment of invention, an air humidifier, in particular an ultrasound evaporator, is arranged in the bypass branch.

The air humidifier may enable, if need be, a selective increase of the air humidity in the air stream.

Moreover, the need may be met by a method which comprises:
  measuring of an actual value of the air humidity in a sample space of the climatic chamber and
  at least partial conveying of the air via a drying branch when the actual value of the air humidity exceeds a predetermined setpoint value for the air humidity in the sample space and/or at least partial conveying of the air via a bypass branch when the actual value of the air humidity reaches or falls below the predetermined setpoint value for the air humidity in the sample space.

It may thus be ensured that a predetermined air humidity and/or temperature is rapidly reached. In addition, once the values for the air humidity and/or the temperature in the sample space are reached, they may be maintained extremely precisely and over long periods.

According to another exemplary embodiment of the method, the air is cooled by the temperature-regulating device when the actual value of the temperature in the sample space exceeds the predetermined setpoint value.

If need be, the air may thus be cooled when the temperature of the air rises for example following the absorption of air humidity in the drying branch on account of the usually exothermic reaction of the desiccant in the form of the zeolites.

According to another exemplary embodiment of the method according to the invention, the air is heated by a temperature-regulating device when a measured actual value of the temperature in the sample space falls below a predetermined setpoint value.

By the optionally provided heating function of the temperature-regulating device via an additional heating device, the temperature of the air in the sample space may, if required, be raised above the ambient air temperature or room temperature independently of the effect of the zeolites, in order for example to reach a predetermined air humidity value which, with a lower air temperature, would lead to an undesired condensation of air humidity.

According to another exemplary embodiment of the method, the air is guided by at least one guide element at least partially through the drying branch and/or at least partially through the bypass branch.

This development may enable a very rapid and yet precise regulation of the air humidity in the sample space by the simple actuation of the guide elements.

Further advantageous developments of the climatic chamber and the method are set out in the claims.

SHORT DESCRIPTION OF THE DRAWINGS

In the drawing:
FIG. 1 shows a diagrammatic representation of the climatic chamber according to an exemplary embodiment of the invention.

DETAILED DESCRIPTION OF AN EXEMPLARY EMBODIMENT

FIG. 1 shows a diagrammatic representation of the mode of functioning of the climatic chamber according to an exemplary embodiment of the invention for rapidly reaching and maintaining a predetermined air humidity and/or a predetermined temperature in a sample space.

Climatic chamber 1 comprises, amongst other things, a sample space 2, a bypass branch 3, and a drying branch 4. A fan 6 is located in the region of an outlet 5 from sample space 2. The fan 6 conveys the air from sample space 2 via an outlet elbow 7 in the direction of the directional arrows represented with continuous lines into drying branch 4, since guide elements 8, 9 in the position symbolised by continuous lines essentially shut off bypass branch 3.

Guide elements 8, 9 can, as shown in FIG. 1, be constituted by flaps. The flaps can be actuated for example by servomotors, actuating motors or other actuators, controlled by a control and regulating device. Instead of the flaps as guide elements 8, 9, other electrical or pneumatically operated shut-off elements, such as for example valves, slide valves, tyre valves or suchlike, can also be used as an alternative.

Three air dehumidifiers 10, 11, 12 are arranged in drying branch 4. A desiccant 13 is present in each case in air dehumidifiers 10, 11, 12. As desiccant 13, use is preferably made of zeolites with a grainy consistency, which bind the absorbed air humidity very tightly to themselves and can be regenerated as often as desired by the supply of heat. Desiccant 13 in the form of zeolites can thus be inserted into air dehumidifiers 10, 11, 12, for example in wide-mesh, readily air-permeable wire baskets. The wire baskets preferably have a cross sectional area which roughly corresponds to the cross-sectional area of drying branch 4, so that the air flows through desiccant 13 as completely as possible and without major flow resistances. The wire baskets with desiccant 13 located therein also enable rapid replaceability of desiccant 13.

After flowing through air dehumidifiers 10, 11, 12, the air is conveyed by a further fan 14 through an inlet elbow 15, a temperature-regulating device 16 and an inlet 17 back into sample space 2. The air thus flows through climatic chamber 1 in an essentially self-contained circuit. A sample 18 to be investigated in the climatic chamber 1 is present in sample space 2.

By temperature-regulating device 16, the air is cooled, if need be, in the region of inlet elbow 15, so that the temperature of the air can be lowered in a selective manner. If temperature-regulating device 16 has an optional heating device, the temperature in sample chamber 2 can also be raised above the level of the ambient air temperature or room temperature independently of the effect of the zeolites.

This may be necessary, for example, when it is intended to establish an air humidity in climatic chamber 1 that lies above the saturation air humidity at the current temperature in sample space 2. In this case, it may be necessary to increase the temperature of the air in a selective manner by the heating device, in order to avoid condensation of air humidity in the climatic chamber 1 at the desired temperature and/or air humidity in sample space 2.

Furthermore, when the zeolites as desiccant 13 absorb moisture, they give off a part of the energy that has been supplied to them by heat during the regeneration. The heat supply during the regeneration of desiccant 13 brings about the complete reversible expulsion of the moisture absorbed by desiccant 13, in particular the water or air humidity, from the crystalline bond of the zeolites. As a result of the absorption of air humidity, the zeolites forming desiccant 13 in air dehumidifiers 10, 11, 12 and also, therefore, the air flowing through desiccant 13 thus heat up, so that the air may have to be cooled down again to the setpoint temperature of, for example, 23° C. by the cooling device contained in temperature-regulating device 16. The cooling function of temperature-regulating device 16 is generally always required, in order to compensate for or even out the temperature fluctuations of the air due to the absorption of air humidity by the zeolites.

Temperature-regulating device 16 can for example be constituted by Peltier elements as a cooling device, which are equally suitable for the heating or the cooling of the air. Alternatively, temperature-regulating device 16 can also comprise a separate heating and cooling device. In this connection, electric heating elements in combination with an absorber cooling device, compressor cooling device or suchlike, are conceivable for constituting the temperature-regulating device. The electric heating elements can be constituted by helically arranged resistance wires or suchlike, for example.

It is not absolutely essential for temperature-regulating device 16 to have the possibility of additional heating of the air flowing through sample space 2 by a heating device. In the case where a heating facility is absent, the air in sample space 2 has a temperature that roughly corresponds to the ambient air temperature and/or room temperature, so that the climatic chamber 1 essentially corresponds in terms of its function to an air dehumidifier with an extremely precise adjustment facility for the degree of air humidity in sample space 2 and not to a climatic chamber.

Temperature-regulating device 16, furthermore, is equipped with a recooler 19 and a further fan 20. The recooler 19 serves in particular to carry away waste heat from the cooling device of temperature-regulating device 16 in the cooling operation. In order to intensify the recooling effect, fan 20 is provided by which, if need be, ambient air is drawn by suction through recooler 19. Furthermore, a control and regulating device 21 is provided.

The air humidity in sample space 2 falls rapidly in the position of guide elements 8, 9 described above, because the air is conveyed almost exclusively via drying branch 4.

If guide elements 8, 9 are swiveled into the position indicated with broken lines, the path for the air through drying branch 4 is essentially cut off. Guide elements 8, 9 move in the direction of the small curved arrows provided on guide elements 8, 9. In this position of guide elements 8, 9, air is conveyed almost exclusively via bypass line 3 along the directional arrows drawn dashed. In this position of guide elements 8, 9, the air humidity in sample space 2 remains essentially unchanged or at least it increases only very slowly, because the air is now essentially conveyed solely via bypass branch 3. A significant increase in air humidity in sample space 2 takes place in this position of guide elements 8, 9 solely in the presence of a sample 18 with a high moisture content and/or with actuation of an optional air humidifier (not shown) by control and regulating device 21.

Furthermore, it is possible for guide elements 8, 9 to assume intermediate positions, so that only a part of the air is conveyed via drying branch 4 or bypass branch 3. A slower and therefore more precise reduction of the air humidity in sample space 2 can thus be achieved. In principle, it is to be assumed that guide elements 8, 9 are moved simultaneously with one another, in order to avoid an undesired backpressure of the air. Alternatively, the guide elements 8, 9 can also be actuated independently of one another. The guide elements 8, 9 are actuated by actuators (not shown), for example servomotors or suchlike.

Bypass branch 3, drying branch 4, outlet elbow 7 and inlet elbow 15 are preferably constituted by pipes or suchlike and represent together with sample space 2 a self-contained circuit in the ideal case completely separated from the ambient air, in which the air is continuously circulated by fans 6, 14 during the period of investigation of the sample. The ambient influence on climatic chamber 1 is thus minimised. In a preferred embodiment of the climatic chamber 1 according to the invention, the pipes have a diameter of less than 200 mm. Instead of the pipes with an essentially circular cross-section described above, use can also be made of air ducts or suchlike which, for example, have a rectangular or square cross-section. Larger diameters than 200 mm are also possible for the pipes.

In the following description, it will be assumed that the temperature in sample space 2 is in principle measured in degrees Celsius (° C.). The air humidity of the air in sample space 2 is determined as relative air humidity in percentage (rel. hum. %). The relative air humidity denotes the ratio in percentage between a maximum quantity of water that can be absorbed in theory by the air at a specific temperature to the quantity of water actually present in the air at the time of the measurement.

At least one air humidity sensor 22 and at least one temperature sensor 23 are preferably arranged in the sample space. The corresponding measured values or actual values of the temperature and air humidity currently prevailing in sample space 2 are ascertained by air humidity sensor 22 and temperature sensor 23 and relayed via measurement lines (not shown) to control and regulating device 21. Alternatively, further air humidity sensors and/or further temperature sensors can be arranged inside or outside sample space 2, in order to enable a more accurate determination of the actual values for the temperature and the air humidity so as to improve the control.

An arrangement of air humidity sensor 22 and temperature sensor 23 diverging from the representation of FIG. 1 is also possible. The air humidity sensor 23 can be arranged for example in the region of inlet elbow 15 or outlet elbow 7. Furthermore, air humidity sensors can be arranged in the region of bypass branch 3 and/or drying branch 4. The same also applies to the arrangement of temperature sensor 23. A divergence deviation from the arrangement of air humidity sensor 22 and temperature sensor 23 in sample space 2 shown by a way of example in FIG. 1 may be required for example in order to adapt to specific test and investigation conditions for sample 18.

Furthermore, climatic chamber 1 according to the invention comprises input devices (not shown) with which setpoint values for the temperature and air humidity to be reached and maintained in sample space 2 can be predetermined by a user. The input devices can for example be rotary regulators, switches, keys or suchlike. Furthermore, the climatic chamber 1 can comprise output devices, for example in the form of analog displays, digital displays, communication interfaces or suchlike, which display for example the current temperature values and air humidity values in sample space 2 for a user. Furthermore, the climatic chamber 1 according to the invention can be equipped with a time-switch device, which for example emits a signal after the lapse of a period, predeterminable by a user, for the desired dwell time of sample 18 in sample space 2.

The control and regulating device 21 controls all the sequences in the climatic chamber 1 according to the invention. For this purpose, guide elements 8, 9, temperature-regulating device 16 and fans 6, 14, 20, amongst other things, are connected via control lines (not shown in FIG. 1) to control and regulating device 21. Corresponding to this, the air humidity sensor 22 and the temperature sensor 23 are also connected via measurements lines to control and regulating device 21. Furthermore, the input devices and output devices for the user are connected to the control and regulating device 21. The control and regulating device 21 is preferably constituted by a standard computing unit, in particular by a digital computer.

The term "rapidly reaching" a predetermined air humidity and/or temperature in sample space 2 means that, with an initial air humidity of, for example, 50% in sample space 2, the air humidity reaches a value of less than 1% within a period of less than 30 seconds after starting up climatic chamber 1. By the climatic chamber 1 according to the invention, this value of the air humidity of less than 1% at a temperature of, for example, 23° C. (room temperature, ambient air temperature) in sample space 2 can in particular be reached rapidly and, in addition, be maintained precisely over the duration of the test, i.e. can be held essentially constant.

All in all, an extremely rapid and at the same time precise adjustment and maintenance of an air humidity in sample space 2 predetermined by the user is in the first place made possible by the climatic chamber 1 according to the invention. For this purpose, temperature-regulating device 16 comprises in the first place a cooling device. Moreover, a temperature in sample space 2 predetermined by the user can be rapidly and precisely reached and maintained with a temperature-regulating device 16 with a facility for beating the air flowing through sample space 2 by a suitable heating device, said temperature also being able to lie above the level of the ambient air temperature or room temperature independently of the influence of the zeolites.

According to the method according to an exemplary embodiment of the invention, a user first predetermines the desired setpoint values for the air humidity and/or the temperature in sample space 2 with the input device. Sample 18 to be investigated is of course first introduced into sample space 2.

The setpoint values predetermined by the user are recorded and stored by the control and regulating device 21. If, for example, a user predetermines a setpoint value of 23° C. for the temperature and a setpoint value of 10% for the relative air humidity in sample space 2 by the input devices, control and regulating device 21 seeks to reach these values as rapidly as possible and then to keep them constant, in particular by actuation of guide elements 8, 9, temperature-regulating device 16 and fans 6, 14. The values currently prevailing in sample space 2, i.e. the actual values for the air humidity and/or the temperature, are continuously determined by the air humidity sensor 22 and the temperature sensor 23 and relayed via measurement lines to the control and regulating device 21.

The precise sequence of the method according to the exemplary embodiment of the invention will be explained below in greater detail with the aid of the control process for the air humidity and the corresponding control process for the temperature using the example of a predetermined air humidity of 10% and a temperature of 23° C., which roughly corresponds to the ambient air temperature or room temperature.

If the value of the current relative air humidity, i.e. the actual value, in sample space 2 amounts for example to 50% initially, guide elements 8, 9 are swiveled by control and regulating device 21 into the position represented by the continuous lines, so that the air flows almost exclusively through drying branch 4. The excess air humidity is now rapidly extracted from the air by the zeolites contained as desiccant 13 in air dehumidifiers 10, 11, 12, so that the air humidity in sample space 2 begins to fall. The current air humidity in sample space 2 is constantly determined by air humidity sensor 22.

Guide elements 8,9 can assume arbitrary "intermediate positions" and are not limited to the completely opened or closed position represented by way of example in the illustration of FIG. 1. The term "intermediate position" means in this connection that a volume flow proportion between 0% in 100% of the total air stream can be conveyed both through bypass branch 3 and drying branch 4 depending on the position of guide elements 8, 9, wherein the sum of the volume flow proportions of the sub-airstreams in drying branch 4 and in bypass branch 3 always amounting to 100%.

The movement of guide elements 8, 9 preferably takes place by so-called "servomotors", which permit arbitrary positions and/or arbitrary "intermediate positions" of guide elements 8, 9, preferably designed as flaps, under the control of control and regulating device 21.

The position of guide elements 8, 9 is varied by control and regulating device 21 during the actual control process until such time as the actual value of the air humidity in sample space 2, apart from a tolerable control deviation, is roughly equal to the predetermined setpoint value of 10% for the air humidity. If sample 18 has a high moisture content, guide elements 8, 9 are also opened wide by control and regulating device 21, in order to reach more rapidly the setpoint value of the air humidity by conveying a large volume flow of air through drying branch 4. If, on the other hand, sample 18 has a lower moisture content, the amplitudes of the movements of guide elements 8, 9 are reduced, controlled by the control and regulating device, in order to avoid overswings of the control process and to reach the setpoint value more rapidly.

Once the setpoint value has been reached, guide elements 8, 9 can be swiveled by control and regulating device 21 into the position represented by the broken line, so that the air is now essentially conveyed exclusively via bypass branch 3 and the air humidity in sample space 2 remains constant.

Preferably, however, guide elements 8, 9 are located in a "middle position" when the setpoint value of the air humidity in sample space 2, minus a control tolerance, has been reached, in order in particular to enable a more rapid compensation with renewed fluctuations of the air humidity.

If the value of the air humidity prevailing in sample space 2 changes again from 10% due to external influences and/or due to the influence of sample 18, the air humidity is again brought to the predetermined setpoint value of 10% by means of drying branch 4 and a corresponding adjustment of guide elements 8, 9, controlled by control and regulating device 21.

If the current value of the temperature of the air in sample space 2 amounts for example to 18° C., this temperature value is determined by temperature sensor 23 and relayed to control and regulating device 21. The actual value of the temperature in sample space 2, minus a control tolerance, is thus smaller than the setpoint value of 23° C. predetermined by the user, so that the air is heated by the temperature-regulating device 16 until such time as the actual value of the temperature again corresponds to the setpoint value of 23° C., minus a control tolerance. An increase in the temperature of the air in sample space 2 above the level of the ambient air temperature or room temperature independently of the effect of the zeolites is as a rule only possible if temperature-regulating device 16, as has already been described above, comprises the optional facility of heating by a heating device, for example in the form of electrically operated heating elements or suchlike.

If the exothermic reaction of the zeolites shall be used for indirect "heating" of the air in sample space 2, it needs to be taken into account that, as a result of this, the air humidity in sample space 2 may possibly again change in an undesired manner.

If, on the other hand, the actual value of the temperature of the air in sample space 2 is greater than the predetermined setpoint value of 23° C., the air is cooled by the cooling device of temperature-regulating device 16 until such time as the setpoint value of the temperature of 23° C., minus a control tolerance, has been reached. In its mode of functioning, the control process for the temperature of the air corresponds in principle to the control process for the air humidity.

Both the control process for the air humidity and the control process for the temperature are controlled in parallel, or matched to one another, by control and regulating device 21. Moreover, it may also be necessary to control, in a suitable manner by the control and regulating device 21, fans 6, 14 which circulate the air inside climatic chamber 1, in order for example to lessen or intensify the drying process in drying branch 4 and/or the heating or cooling of the air in temperature-regulating device 16. This control of fans 6, 14 can take place for example by a speed regulator and/or an adjustment of the setting angle of the fan rotors. The same applies to fan 20.

The overall control process is relatively expensive on account of the control processes for the air humidity and the temperature to be performed in parallel, so that the implementation of the control takes place preferably using software by the control and regulating device 21. Alternatively, the control can also take place with analog circuits.

On account of the forced circulation of the air by the fans 6, 14 in combination with the rapid change-over facility between bypass branch 3 and drying branch 4, it is possible by the method according to the invention for a temperature and/or air humidity in climatic chamber 1 predetermined by the user to be maintained quickly and in addition very precisely over the whole test duration, i.e. to be held constant for the most part.

It should be noted that the term "comprising" does not exclude other elements or steps and the "a" or "an" does not exclude a plurality. Also elements described in association with different embodiments may be combined. It should also be noted that reference signs in the claims shall not be construed as limiting the scope of the claims.

LIST OF REFERENCE SIGNS 1 climatic chamber
2 sample space
3 bypass branch
4 drying branch
5 outlet
6 fan
7 outlet elbow
8 guide element
9 guide element
10 air dehumidifier
11 air dehumidifier
12 air dehumidifier
13 desiccant
14 fan
15 inlet elbow
16 temperature-regulating device
17 inlet
18 sample
19 recooler
20 fan
21 control and regulating device
22 air humidity sensor
23 temperature sensor

The invention claimed is:

1. A climatic chamber for rapidly reaching and maintaining a predetermined air humidity and/or a predetermined temperature, comprising at least one fan wherein the air in a sample space is conveyable by said at least one fan from an outlet of the sample space at least partially via at least one of a bypass branch and a drying branch back to an inlet of the sample space, wherein the air can be guided by at least one guide element at least partially via at least one of the bypass branch and the drying branch, wherein the guide elements are actuable by a control and regulating device depending on at least one of a measured actual value of the air humidity and a measured actual value of the temperature.

2. The climatic chamber according to claim 1, wherein, in order to rapidly reach and maintain a predetermined setpoint value for the temperature in the sample space, the temperature of the air is variable by a heating and/or cooling device, wherein the temperature-regulating device being arranged in the region of the inlet.

3. The climatic chamber according to claim 1, wherein at least one air dehumidifier for drying the air is arranged in the drying branch.

4. The climatic chamber according to claim 3, wherein the air dehumidifiers contain a desiccant.

5. The climatic chamber according to claim 1, wherein an ultrasound evaporator is arranged in the bypass branch.

6. The climatic chamber according to claim 1, wherein at least one air humidity sensor for determining the actual value of the air humidity in the sample space is arranged in the region of the sample space.

7. The climatic chamber according to claim 1, wherein at least one temperature sensor for determining the actual value of the temperature in the sample space is arranged in the region of the sample space.

8. The climatic chamber according to claim 1, wherein the drying branch and the bypass branch and the sample space form substantially closed circuit for the circulation of the air, wherein the drying branch and the bypass branch comprise closed conduits.

9. The climatic chamber according to claim 1, wherein the air can be circulated continuously by the fans in a closed circuit.

10. A method for rapidly reaching and maintaining a predetermined air humidity and/or a predetermined temperature in a climatic chamber comprising:
    measuring an actual value of the air humidity in a sample space of a climatic chamber, the climatic chamber comprising at least one fan wherein the air in a sample space is conveyable by said at least one fan from an outlet of the sample space at least partially via at least one of a bypass branch and a drying branch back to an inlet of the sample space, wherein the air can be guided by at least one guide element at least partially via at least one of the bypass branch and the drying branch, wherein the guide elements are actuable by a control and regulating device depending on at least one of a measured actual value of the air humidity and a measured actual value of the temperature; and
    at least partially conveying the air via at least one of drying branch when the actual value of the air humidity exceeds a predetermined setpoint value for the air humidity in a sample space of the climatic chamber and the bypass branch when the actual value of the air humidity reaches or falls below the predetermined setpoint value for the air humidity in the sample space.

11. The method according to claim 10, wherein the air is cooled by a temperature-regulating device when the actual value of the temperature in the sample space exceeds the predetermined setpoint value for the temperature in the sample space.

12. The method according to claim 10, wherein the air is heated by the temperature-regulating device when the measured actual value of the temperature in the sample space falls below a predetermined setpoint value for the temperature in the sample space.

13. The method according to claim 10, wherein the actual value of the air humidity in the region of the sample space is measured with at least one air humidity sensor.

14. The method according to claim 10, wherein the actual value of the temperature in the region of the sample space is measured with at least one temperature sensor.

15. The method according to claim 10, wherein the air is guided by at least one guide element at least partially through the drying branch and/or at least partially through the bypass branch.

16. The method according to claim 10, wherein guide elements are actuated by a control and regulating device depending on the predetermined setpoint values for at least one of the temperature and the air humidity in the sample space as well as the measured actual values of at least one of the air humidity and/or the temperature in the sample space.

17. The method according to claim 10, wherein at least one of the fans and the temperature regulating device are controlled depending on the predetermined setpoint values for at least one of the temperature and/or the air humidity in the sample space as well as the measured actual values of at least one of the air humidity and/or the temperature in the sample space.

18. The method according to claim 10 wherein the air is circulated continuously by at least one fan from an outlet of the sample space at least partially via at least one of the bypass branch and the drying branch back to an inlet of the sample space in a substantially closed circuit.

* * * * *